(12) United States Patent
Bhandari et al.

(10) Patent No.: US 10,337,993 B2
(45) Date of Patent: Jul. 2, 2019

(54) METHODS AND APPARATUS FOR FLUORESCENCE LIFETIME IMAGING WITH PERIODICALLY MODULATED LIGHT

(71) Applicant: Massachusetts Institute of Technology, Cambridge, MA (US)

(72) Inventors: Ayush Bhandari, Cambridge, MA (US); Christopher Barsi, Lee, NH (US); Achuta Kadambi, Cambridge, MA (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 183 days.

(21) Appl. No.: 15/487,435

(22) Filed: Apr. 14, 2017

(65) Prior Publication Data

US 2018/0259454 A1    Sep. 13, 2018

Related U.S. Application Data

(60) Provisional application No. 62/323,621, filed on Apr. 15, 2016.

(51) Int. Cl.
*G01N 21/64*    (2006.01)
*G07D 7/00*    (2016.01)

(52) U.S. Cl.
CPC ..... *G01N 21/6408* (2013.01); *G01N 21/6456* (2013.01); *G07D 7/00* (2013.01); *G01N 2201/0691* (2013.01); *G01N 2201/126* (2013.01); *G01N 2201/129* (2013.01)

(58) Field of Classification Search
CPC .................. G01N 21/6408; G01N 21/6465
See application file for complete search history.

(56) References Cited

U.S. PATENT DOCUMENTS

| | | | |
|---|---|---|---|
| 6,323,942 B1 | 11/2001 | Bamji | |
| 6,515,740 B2 | 2/2003 | Bamji et al. | |
| 6,587,186 B2 | 7/2003 | Bamji et al. | |
| 6,678,039 B2 | 1/2004 | Charbon | |

(Continued)

OTHER PUBLICATIONS

"Resolving Multi-path Interference in Time-of-Flight Imaging via Modulation Frequency Diversity and Sparse Regularization", Optics Letters, vol. 39, issue 6, Apr. 3, 2014 to Bhandari et al.*

(Continued)

*Primary Examiner* — Kenneth J Malkowski
(74) *Attorney, Agent, or Firm* — Stephen R. Otis

(57) ABSTRACT

A light source may illuminate a scene with amplitude-modulated light. The scene may include fluorescent material. The amplitude modulation may be periodic, and the frequency of the amplitude modulation may be swept. During the sweep, a time-of-flight sensor may take measurements of light returning from the scene. A computer may calculate, for each pixel in the sensor, a vector of complex numbers. Each complex number in the vector may encode phase and amplitude of light incident at the pixel and may correspond to measurements taken at a given frequency in the sweep. A computer may, based on phase of the complex numbers for a pixel, calculate fluorescence lifetime and scene depth of a scene point that corresponds to the pixel.

4 Claims, 6 Drawing Sheets

(56) References Cited

U.S. PATENT DOCUMENTS

| | | |
|---|---|---|
| 6,777,659 B1 | 8/2004 | Schwarte |
| 6,825,455 B1 | 11/2004 | Schwarte |
| 7,012,738 B1 | 3/2006 | Schwarte |
| 7,060,957 B2 | 6/2006 | Lange et al. |
| 7,262,402 B2 | 8/2007 | Niclass et al. |
| 7,361,883 B2 | 4/2008 | Xu et al. |
| 7,405,812 B1 | 7/2008 | Bamji |
| 7,408,627 B2 | 8/2008 | Bamji et al. |
| 7,508,505 B2 | 3/2009 | Lustenberger et al. |
| 7,636,150 B1 | 12/2009 | McCauley et al. |
| 7,671,391 B2 | 3/2010 | Kawahito |
| 7,719,662 B2 | 5/2010 | Bamji et al. |
| 8,194,233 B2 | 6/2012 | Bamji |
| 8,294,882 B2 | 10/2012 | Van Der Tempel et al. |
| 8,314,924 B2 | 11/2012 | Bamji et al. |
| 8,355,117 B2 | 1/2013 | Niclass |
| 8,786,678 B2 | 7/2014 | Schmidt et al. |
| 8,953,149 B2 | 2/2015 | Bamji |
| 9,007,579 B2 | 4/2015 | Westphal |
| 9,516,244 B2 | 12/2016 | Borowski |
| 2014/0340569 A1 | 11/2014 | Raskar et al. |
| 2015/0120241 A1 | 4/2015 | Kadambi et al. |

OTHER PUBLICATIONS

"Coded Time-of-Flight Imaging Calibration Free Fluorescence Lifetime Estimation" Imaging and Applied Optics, 2014 to Bhandari et al.*

Buttgen, B., et al., CCD/CMOS Lock-In Pixel for Range Imaging: Challenges, Limitations and State-of-the-Art; published in Proceedings of 1st Range Imaging Research Day (2005).

Foix, S., et al., Lock-in Time-of-Flight (ToF) Cameras: A Survey; published in IEEE Sensors Journal, vol. 11, Issue 9 (Sep. 2011).

Lange, R., 3D Time-of-Flight Distance Measurement with Custom Solid-State Image Sensors in CMOS/CCD-Technology; PhD dissertation; University of Siegen (2000).

Niclass, C., et al., Single-Photon Synchronous Detection; published in IEEE Journal of Solid-State Circuits, vol. 14, Issue 7, pp. 1977-1989 (2009).

Payne, A., et al., Multiple frequency range imaging to remove measurement ambiguity; published in Proceedings of 9th Conference on Optical 3-D Measurement Techniques, Jul. 1-3, 2009, Vienna, Austria (pp. 139-148). Vienna, Austria: Vienna University of Technology.

Ringbeck, T., A 3D Time of Flight Camera for Object Detection; published in Optical 3-D Measurement Techniques, Jul. 9-12, 2007 ETH Zurich, Plenary Session 1: Range Imaging I (2007).

Spirig, T., et al., The Lock-In CCD—Two-Dimensional Synchronous Detection of Light; published in IEEE Journal of Duantum Electronics, vol. 31, Issue 9, pp. 1705-1708 (1995).

Chan, J., et al., Digitally synthesized beat frequency-multiplexed fluorescence lifetime spectroscopy; published in Biomedical Optics Express, vol. 5, No. 12, pp. 4428-4436 (2014).

Coleman, T., et al., An Interior Trust Region Approach for Nonlinear Minimization Subject to Bounds; published in SIAM J. Optim., vol. 6, No. 2, pp. 418-445 (May 1996).

Esposito, A. et al., All-solid-state lock-in imaging for wide-field fluorescence lifetime sensing; published in Optics Express, vol. 13, No. 24, pp. 9812-9821 (2005).

Gratton, E., et al., Resolution of mixtures of fluorophores using variable-frequency phase and modulation data; published in Biophysical Journal, vol. 46, No. 4, pp. 479-486 (Oct. 1984).

Hanley, Q., et al., Fluorescence lifetime imaging: multi-point calibration, minimum resolvable differences, and artifact suppression; published in Cytometry, vol. 43, No. 4, pp. 248-260 (Apr. 2001).

Horiuchi, N., Counterfeiting: The fluorescence of fraud; published in Nature Photonics, vol. 4, p. 72 (2010).

Kadambi, A., et al., Resolving multipath interference in time-of-flight imaging via modulation frequency diversity and sparse regularization; published in Optics Letters, vol. 39, Issue 6, pp. 1705-1708 (2014).

Pancheri, L., et al., SPAD Image Sensor With Analog Counting Pixel for Time-Resolved Fluorescence Detection; published in IEEE Transactions on Electron Devices, vol. 60, No. 10 (Oct. 2013).

Bhandari, A., Coded Time-of-Flight Imaging for Calibration Free Fluorescence Lifetime Estimation; published in OSA Technical Digest (online) (Optical Society of America, 2014), paper IW2C.5, proceedings of Imaging Systems and Applications 2014.

* cited by examiner

BASED ON MEASUREMENTS TAKEN BY A ToF SENSOR, A COMPUTER MAY, AMONG OTHER THINGS:

(A) CALCULATE, FOR EACH GIVEN PIXEL IN THE ToF SENSOR, DISTANCE $d$ AND FLUORESCENCE LIFETIME $\tau$, RESPECTIVELY, OF A SCENE POINT THAT CORRESPONDS TO THE GIVEN PIXEL;

(B) OUTPUT AN AMPLITUDE IMAGE;

(C) OUTPUT A PHASE IMAGE;

(D) OUTPUT A DEPTH MAP;

(E) OUTPUT A FLUORESCENCE LIFETIME MAP; OR (F) IDENTIFY ONE OR MORE MATERIALS (e.g., FLUORESCENT MATERIALS) IN THE SCENE.

FIG. 6

METHODS AND APPARATUS FOR FLUORESCENCE LIFETIME IMAGING WITH PERIODICALLY MODULATED LIGHT

RELATED APPLICATIONS

This application claims the benefit of U.S. Provisional Application No. 62/323,621, filed Apr. 15, 2016 (the "Provisional Application"). The entire disclosure of the Provisional Application is herein incorporated by reference.

STATEMENT REGARDING FEDERALLY SPONSORED RESEARCH OR DEVELOPMENT

This invention was made with Government support under Contract No. N00030-13-C-0005 awarded by the Department of the Navy. The Government has certain rights in the invention.

FIELD OF TECHNOLOGY

The present invention relates generally to fluorescence lifetime imaging.

COMPUTER PROGRAM LISTING

Attached are three computer program files, each created as a .txt file on Feb. 22, 2017: (1) OpticaDataProcess.txt with a size of about 2 KB; (2) createFit.txt with a size of about 3 KB; and (3) FDToF_optica.txt with a size of about 2 KB. These three computer program files comprise source code for software employed in a prototype implementation of this invention.

BACKGROUND

Conventional fluorescence lifetime imaging ("FLI") suffers from at least two technical problems.

First, conventional FLI may require precise knowledge of the shape of the light waveform emitted by the FLI system to illuminate the scene. It is challenging to obtain a precise knowledge of the shape of the light waveform emitted by the FLI system, because physical processes (e.g., crosstalk, latency, electromagnetic interference, hysteresis, nonlinear responses, or signal noise) in electronics or other circuitry (e.g., in a computer, driver, light source, or wiring) may distort the shape (e.g., phase or amplitude) of the emitted light signal, relative to the shape of the electric control signal that is generated by a timer to control the lighting. For example, the electric control signal generated to control the lighting may be a square wave, but the actual emitted light waveform may be smoothed and curved. Such smoothing occurs in most electro-optical systems that tend to be low-pass systems that suppress high frequency components. In a conventional ToF system, in order to achieve precise knowledge of the shape of the light waveform that is emitted by the system, expensive equipment may be employed. This expensive equipment may be limited to a first mode (e.g., pulsed illumination with non-periodic pulses) or limited to a second mode (e.g., periodically modulated illumination, such as sinusoidal or square wave modulation), and thus (2) may be unable to function in both modes. As a result, conventional FLI cannot be performed by a general purpose, inexpensive consumer grade time-of-flight ("ToF") camera.

Second, conventional FLI may require taking one or more calibration measurements to determine the placement of the fluorescent sample relative to the sensor. The distance or depth of the sample with respect to the sensor is an unknown that is typically calibrated. Typically, this calibration is repeated often, since a separate calibration is performed for each different scene being imaged. This repetitive, time-consuming calibration is not desirable.

SUMMARY

In illustrative implementations of this invention, these two technical problems are solved. In illustrative implementations, the FLI system accurately measures fluorescence lifetime: (a) even though the precise shape of the excitation light waveform is not known; and (b) even without calibration at a known scene depth.

Put differently, in illustrative implementations, the FLI system accurately measures fluorescence lifetime even though the system may be—loosely speaking—"blind" (i.e., the precise shape of the excitation light waveform is not known) and "reference-free" (i.e., scene depth has not been previously determined by one or more separate calibration measurements). Because the FLI imaging system can accurately measure fluorescence lifetime while operating "blind" and "reference-free", the system may be implemented with an inexpensive, consumer-grade lock-in ToF sensor and without spending time for distance calibration.

In illustrative implementations, a light source emits amplitude-modulated light. The light emitted by the light source illuminates a scene and excites a fluorescent material in the scene. In response to this excitation light, the fluorescent material emits fluorescent light that travels to a lock-in ToF sensor. The lock-in ToF sensor measures incident light, including this fluorescent light. In some cases, a bandpass filter (e.g., a bandpass dielectric filter) is positioned in front of the lock-in ToF sensor and filters out excitation light that reflects from the scene, such that the incident light reaching the ToF sensor comprises fluorescent light (from the fluorescing material in the scene) and noise (such as ambient light).

In illustrative implementations, the FLI system determines, for each pixel of the lock-in ToF sensor, respectively, the fluorescence lifetime and scene depth for a point in the scene that corresponds to the pixel.

In illustrative implementations: (A) the amplitude-modulated light waveform is periodic (such as sinusoidal wave or a square wave); and (B) a computer calculates, for each pixel of the lock-in ToF sensor, respectively, the fluorescence lifetime and scene depth for a point in the scene that corresponds to the pixel, by computing a closed form solution or by computing a non-linear least squares solution or other non-linear inverse solution.

Alternatively, in some implementations: (A) the amplitude-modulated light waveform comprises a binary coded pulsed signal, where the pulses are not periodic (such as a maximum length sequence or Gold sequence); and (B) a computer calculates, for each pixel of the lock-in ToF sensor, respectively, the fluorescence lifetime and scene depth for a point in the scene that corresponds to the pixel, by computing a non-linear least squares solution.

In some implementations, the FLI system is configured: (A) to operate in either a periodic illumination mode (in which amplitude modulation of the excitation waveform is periodic, such as a sinusoidal or square wave) or a pulsed illumination mode (in which the excitation waveform is a binary coded, pulsed signal, in which the pulses are not periodic); and (B) to switch between these two modes by, among other things (i) changing the control signal that controls amplitude modulation of light emitted by the light source, and (ii) changing an algorithm used to process the measurements taken by the ToF sensor This invention has many practical applications, including (a) microscopy; and (b) large-scale fluorescence lifetime estimation, such as for detection of counterfeit banknotes.

The Summary and Abstract sections hereof: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the description of this invention in the Field of Technology section is not limiting; instead it identifies, in a general, non-exclusive manner, a field of technology to which some implementations of this invention generally relate.

BRIEF DESCRIPTION OF THE DRAWINGS

In FIG. 2, depth and lifetime are obtained by either a closed-form solution or by a non-linear least squares solution. In FIG. 3, depth and lifetime are obtained by a non-linear least squares solution. In FIG. 4, depth and lifetime are obtained from a closed form solution.

FIG. 6 shows an FLI method.

The above Figures show some illustrative implementations of this invention, or provide information that relates to those implementations. The examples shown in the above Figures do not limit this invention. This invention may be implemented in many other ways.

DETAILED DESCRIPTION

Illustrative Hardware

Figure 1:
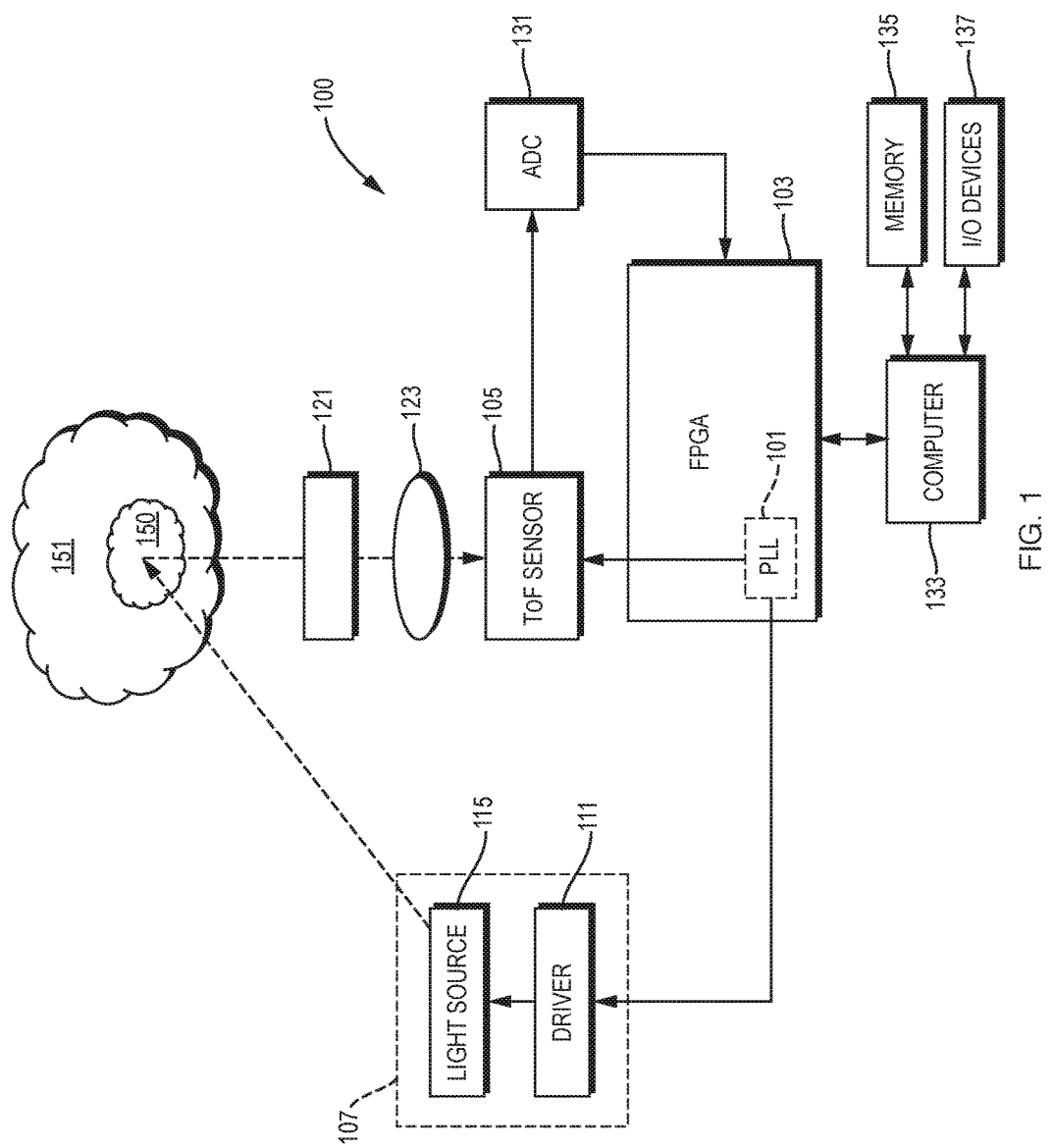
FIG. 1 shows hardware for an FLI system.

FIG. 1 shows hardware for an FLI system 100, in an exemplary implementation of this invention. In FIG. 1, an illumination system 107 illuminates a s scene 151 that includes a fluorescent material 150. An FPGA (field-programmable gate array) integrated circuit 103 may generate control signals that are communicated, via a PLL (phase-locked-loop) 101, to a time-of-flight sensor 105 and also to a driver 111 in illumination system 107. The driver 111 may in turn control a light source 115 and thus controls amplitude modulation of light emitted the light source 115.

The amplitude-modulated light emitted by the light source 115 may comprise a periodic, continuous-wave signal (such as a sine wave or a square wave) or may comprise a coded, binary, pulsed light signal in which the pulses are not periodic (such as a maximum length sequence or a Gold sequence). The light source 115 may comprise, for example, one or more LEDs (light-emitting diodes), lasers, electronic white light sources, or supercontinuum light sources. For example, the light source 115 may emit coherent light, incoherent light, collimated light or uncollimated light. The spectrum of light emitted by the light source may peak in a fluorescence absorption band of the fluorescent material 150.

Light that travels from the scene 151 in the direction of ToF sensor 105 may include both (1) reflected excitation light (i.e., light from the light source 115 that reflects from the scene) and (2) fluorescent light emitted by the fluorescent material 150, due to fluorescence that occurs in response to light from light source 115 striking the fluorescent material 150. A filter 121 may filter out reflected excitation light. For example, the filter 121 may comprise a dielectric filter. The filter 121 may comprise a bandpass, lowpass or hi-pass filter.

Optics 123 may focus light onto a sensor pixel array of the ToF sensor 105. For example, optics 123 may comprise one or more lens, mirrors or other refractive or reflective optical elements.

The ToF sensor 105 may comprise a lock-in ToF sensor, which includes an array of lock-in pixels. For example, the pixels in the ToF sensor 105 may comprise: (a) CMOS-CCD lock-in pixels, or (b) PMD (photonic mixer device) pixels. Also, for example, each pixel in the ToF sensor may comprise a so-called "1-tap" pixel, a so-called "2-tap" pixel, a so-called "4-tap" pixel, or a so-called "n-tap" pixel. Also, for example, the ToF sensor 105 may comprise a time-of-flight sensor described in a Listed patent (as that term in defined herein) or may include sensor pixels described in a Listed patent. The pixels of the ToF sensor 105 may output analog signals that encode measurements taken by the ToF sensor 105.

Alternatively, the pixels of the ToF sensor 105 may output digital signals that encode measurements taken by the ToF sensor 105. For example, in some cases, each pixel of the ToF sensor 105 performs single-photon synchronous detection (SPSD). SPSD involves measurements with single-photon avalanche diodes (SPADs).

The lock-in ToF sensor 105 may take measurements of incident light and may output analog signals that encode these measurements. An ADC (analog-to-digital-converter) 131 may convert these analog signals into digital signals. The FPGA may receive this digitized measurement data and may send this data to a computer 133. The computer 133 may perform an algorithm that recovers, for each pixel in the lock-in ToF sensor, the fluorescence lifetime and distance of a scene point that corresponds to the pixel. The computer 133 may store and retrieve data from memory device 135. The computer 133 may interface with human user(s) via one or more input/output devices 137, such as a keyboard, mouse, display screen, interactive touch display screen, microphone, speaker, or haptic transceiver.

This invention is not limited to the hardware and hardware configuration shown in FIG. 1. This invention may be implemented in many other ways.

In illustrative implementations, the FLI system may be configured for homodyne detection, in the sense that the ToF sensor may compare (e.g., cross-correlate) an electric reference signal and a light signal incident on the ToF sensor, where each of these signals is ultimately derived from the same electronic timer signal.

Periodic Illumination Mode

As noted above, in some implementations, the FLI system (e.g., 100) operates in a periodic illumination mode. While operating in periodic illumination mode, the light emitted by the light source (e.g., 115) may be an amplitude-modulated periodic signal, such as a sine wave, square wave or other AMCW (amplitude-modulated continuous wave) signal.

For example, in some implementations, while operating in periodic illumination mode, the FLI system (e.g., 100) may probe the scene by illuminating the scene with a light signal p(t), the amplitude of which is periodically modulated. For example, the amplitude-modulated light signal p(t) may be a sinusoidal signal (e.g., an AMCW light signal) of form $$p(t) = 1 + p_0 \cos(\omega t) \qquad \text{Equation 1}$$

where $p_0$ is amplitude of the modulated light signal and $\omega$ is angular frequency of the amplitude modulation. More generally, while operating in periodic illumination mode, the amplitude-modulated light signal p(t) may be any periodic signal p(t)=p(t+T), where T is the time period or repetition period. For example, p(t) may comprise a square wave or a triangular wave.

The reflected signal may be given by $$r(t)=(p*=h_{SI})=|\hat{h}(0)|+|\hat{h}(\omega)|p_0\cos(\omega t+\angle\hat{h}(\omega))) \quad \text{Equation 2}$$

where (1) t is time, (2) $h_{SI}$=h(t) is the time-dependent, shift-invariant scene response function, and (3) $\hat{h}(\omega)$ is the Fourier Transform of h(t).

In some implementations, when imaging fluorescence from a scene, h(t) is the fluorescent response at depth d meters using the time-dependent function, $$h_{SI}(t) = h(t) = \rho\delta(t-t_0) + \mu e^{-\frac{t-t_0}{\tau}}\Pi(t-t_0)$$

where (1) $t_0$=2d/c is the round trip, time delay due to an object or a sample at distance d from the sensor, (2) c is the speed of light, (3) $\rho$ is albedo, (4) $\mu$ is luminance of fluorescence, (5) $\tau$ is the fluorescent lifetime and (6) $\Pi$(t) is the Heaviside function. Alternatively, $\mu$ may be any other measure of intensity of fluorescent light.

The reflected signal may be cross-correlated by a lock-in ToF sensor (e.g., 105), resulting in measurements, $$m(t) = |\hat{h}(0)| + |\hat{h}(\omega)|\frac{p_0^2}{2}\cos(\omega t - \angle\hat{h}(\omega)) \quad \text{Equation 3}$$

Next, the lock-in ToF sensor may estimate the amplitude and depth/phase information based on a so-called "four bucket" method. In the four-bucket method, the lock-in ToF sensor may record four equidistant measurements m($\pi$k/2$\omega$), k=0, 1, 2, 3. A computer may use these measurements to compute intermediate values $$M_\omega^{0,2} = m(0) - m\left(\frac{\pi}{\omega}\right) \text{ and } M_\omega^{3,1} = m\left(\frac{3\pi}{2\omega}\right) - m\left(\frac{\pi}{2\omega}\right),$$

and may in turn use these intermediate values to calculate a complex number $z_\omega$, where $$z_\omega = M_\omega^{0,2} + j M_\omega^{3,1}. \quad \text{Equation 4}$$

In some implementations of this invention, the FLI system may operate in periodic illumination mode and a complex number $z_\omega$ may be calculated in accordance with Equation 4 for each pixel of the lock-in ToF camera, for each frequency $\omega$ of amplitude modulation in the sweep. For a given modulation frequency $\omega=\omega_0$, amplitude and phase estimates may be calculated according to $$\underbrace{|\hat{h}(\omega_0)| \approx |z(\omega_0)|/p_0^2}_{\text{Amplitude Estimate}} \text{ and } \underbrace{\angle\hat{h}(\omega_0) \approx \angle z(\omega_0)}_{\text{Phase Estimate}}, \quad \text{Equation 5}$$

respectively.

In Equation 5, the estimation of amplitude $|\hat{h}(\omega_0)|$ depends on $p_0$, where (as noted above) $p_0$ is amplitude of the modulated light signal. However, in Equation 5 phase may be calculated by $\angle\hat{h}(\omega_0) \approx \angle z_{\omega_0}$, without precise knowledge of the shape of light signal $p_0$ (except for frequency). This is advantageous, because the unknowns that we seek to recover in some implementations, namely, lifetime and depth parameters, may be extracted from phase without having to estimate amplitude $|\hat{h}(\omega_0)|$, as discussed in more detail below.

As noted above, conventional FLI systems may require both (a) precise knowledge of the illumination waveform and (b) repeated calibrations for depth. In contrast, in some implementations of this invention, the FLI system, may be loosely said to be operating "blind", in that the FLI system may accurately estimate depth and fluorescence lifetime, regardless of whether the exact shape of the illumination waveform emitted by the system's active light source (e.g., 115) is known in advance. Specifically: In some implementations of this invention, when the FLI system is operating in in periodic illumination mode: (A) the frequency of the amplitude modulation of the illumination light signal waveform is known (because the FPGA and PLL are controlling the frequency), and (B) phase of the amplitude modulation of the illumination light signal is not known in advance from separate calibration measurements, but is instead extracted from the same set of ToF sensor measurements as the fluorescence lifetime. (Specifically, in some implementations, the phase is extracted from a set of ToF sensor measurements, and fluorescence lifetime and scene depth are calculated based on the phase, and thus the phase, lifetime and scene depth are extracted from the same set of ToF sensor measurements). This is in contrast to conventional FLI, in which phase of the amplitude modulation may be known in advance by separate calibration measurements, and this known phase may be used to help extract fluorescence lifetime from a later, separate set of ToF sensor measurements.

Furthermore, in some implementations of this invention, when the FLI system is operating in periodic illumination mode, the amplitude of the modulation of the illumination light signal is not known in advance from separate calibration measurements, but instead the phase, lifetime and amplitude may be extracted from the same set of ToF sensor measurements. This is in contrast to conventional FLI, in which the precise amplitude of the modulation may be known in advance.

In some implementations of this invention, while the FLI system is operating in periodic illumination mode, measurements at multiple frequencies (of amplitude modulation) may be used to estimate depth d and fluorescence lifetime $\tau$.

For example, in some implementations of this invention: (a) the frequency of amplitude modulation of the light is swept; and (b) for each pixel in the lock-in ToF sensor, a computer computes a vector z, where each element of the vector z respectively, is a complex number that (i) is computed based on measurements of incident light taken by the pixel at a particular frequency of amplitude modulation, and (ii) encodes phase and amplitude of light incident on the pixel.

In some implementations, a computer may, for each pixel in the ToF sensor: (1) compute the phase of vector z to produce a vector $\angle$ z, such that each element of vector $\angle$ z is the phase of the corresponding element of vector z; and (2) based on vector $\angle$ z, compute fluorescence lifetime and depth of a scene point that corresponds to the pixel.

Each element in the vector z may correspond to a different frequency in a sweep. For example, in some implementations when the FLI system is operating in periodic illumination mode: (1) the frequency of amplitude modulation of the light may be swept; and (2) each complex value $z_\omega$, respectively, in the vector z is computed based on measurements taken at a frequency $\omega$.

For example, in some implementations, the frequency of amplitude modulation of the light is swept, and, for each pixel in the lock-in ToF sensor: (1) a vector of measurements $m_\omega$ is acquired for each frequency $\omega$ of amplitude modulation in the sweep; (2) a computer calculates a vector z, where each element $z_\omega$, respectively, in vector z is a complex number that encodes phase and amplitude of light incident on the pixel and that is computed based on a vector of measurements $m_\omega$ acquired at a frequency $\omega$; (4) a computer calculates the phase of vector z to produce a vector $\sphericalangle z$, such that each element of vector $\sphericalangle z$ is the phase of the corresponding element of vector z; and (5) based on vector $\sphericalangle z$, a computer calculates fluorescence lifetime and depth of a scene point that corresponds to the pixel.

The number of measurements taken at a given frequency (of amplitude modulation) by a pixel may vary, depending on the particular implementation of this invention. For example, in some implementations: (a) a "four bucket" calculation is used in an interim step; (b) each pixel takes four measurements for each frequency $\omega$ of amplitude modulation, and (c) the vector of measurements $m_\omega$ for a given pixel for a given frequency $\omega$ consists of four measurements and is $$m_\omega = \begin{bmatrix} m(0) & m(\frac{\pi}{2\omega}) & m(\frac{\pi}{\omega}) & m(\frac{3\pi}{2\omega}) \end{bmatrix}.$$

Likewise, in some implementations: (a) each pixel takes two measurements for a given frequency $\omega$ of amplitude modulation, and thus (b) the vector of measurements $m_\omega$ for a given pixel for a given frequency $\omega$ consists of two measurements. More generally, in some implementations: (a) each pixel takes Y measurements for a given frequency $\omega$ of amplitude modulation; and thus (b) the vector of measurements $m_\omega$ for a given frequency $\omega$ for a given pixel consists of Y measurements.

In some implementations, the frequency of amplitude modulation is swept in equal increments of frequency. For example, in some implementations: (1) the frequency of amplitude modulation is swept in equal increments of frequency, such that the frequencies in the sweep are $\omega = n\omega_0$, $n=a, \ldots, N+a-1$, where N is the number of frequencies in the sweep, a is an integer greater than or equal to zero, and $\omega_0$ is a frequency of amplitude modulation; and (2) for each pixel of the ToF sensor, respectively (i) a computer calculates a vector z of complex numbers, (ii) each element of vector z corresponds to a different frequency in the sweep, (iii) $z=|z_{a\omega_0} z_{(a+1)\omega_0} z_{(a+2)\omega_0} \ldots z_{(N+a-1)\omega_0}|$, (iv) each complex number $z_\omega$, respectively, in the vector z encodes phase and amplitude of light incident on the pixel and is computed based on a vector of measurements $m_\omega$ taken by the pixel at a frequency $\omega$, (v) a computer calculates the phase of vector z to produce a vector $\sphericalangle z$, such that each element of vector $\sphericalangle z$ is the phase of the corresponding element of vector z; and (vi) based on vector $\sphericalangle z$, a computer calculates fluorescence lifetime and depth of a scene point that corresponds to the pixel.

In some implementations, a "four bucket" calculation is employed in an interim step. For example, in some implementations, the frequency of amplitude modulation is swept and, for each given pixel in the ToF sensor: (1) the vector of measurements $m_\omega$ for a given frequency $\omega$ consists of four measurements and is $$m_\omega = \begin{bmatrix} m(0) & m(\frac{\pi}{2\omega}) & m(\frac{\pi}{\omega}) & m(\frac{3\pi}{2\omega}) \end{bmatrix};$$

(2) each complex value $z_\omega$, respectively, in the vector z is computed, based on a vector of measurements $m_\omega$ taken at a frequency $\omega$; (3) each complex value $z_\omega$, respectively, in the vector z is estimated by a "four bucket" method according to Equation 4; (4) each complex value $z_\omega$, respectively, in the vector z encodes phase and amplitude of light incident on the pixel; (5) a computer calculates the phase of vector z to produce a vector $\sphericalangle z$, such that each element of vector $\sphericalangle z$ is the phase of the corresponding element of vector z and (6) based on vector $\sphericalangle z$, a computer calculates fluorescence lifetime and amplitude of light incident on the pixel. Alternatively, in step (3) of the preceding sentence, a computer may perform one or more other conventional ToF calculations (instead of a "four bucket" calculation according to Equation 4) to estimate (based on the vector of complex values $m_\omega$ taken at frequency $\omega$) each complex value $z_\omega$, respectively, in the vector z.

In some implementations of this invention: (a) an FLI system operates in periodic illumination mode; (b) the frequency of amplitude modulation is swept in equal increments such that, in each increment of the sweep, frequency changes by $\omega_0$, and (c) for each pixel of the ToF sensor, a computer calculates scene depth d and fluorescence lifetime $\tau$ (of a scene point that corresponds to the pixel) by solving a non-linear inverse problem.

For example, in some implementations, while the FLI system is operating in periodic illumination mode, a computer may (for each pixel of the ToF sensor) calculate scene depth d and fluorescence lifetime $\tau$ (of a scene point that corresponds to the pixel) by solving a non-linear least squares problem according to $$\underset{\{d,\tau\}}{\mathrm{argmin}} \sum_{n=a}^{N+a-1} \left| \sphericalangle z_{n\omega_0} + 2\left(\frac{d}{c}\right) n\omega_0 + \tan^{-1}(n\omega_0 \tau) \right|^2 \quad \text{Equation 6}$$

where (1) N is the number of frequencies of amplitude modulation in the sweep; (2) a is an integer that is greater than or equal to zero; (3) $\omega_0$ is a frequency of amplitude modulation, (4) each $z_{n\omega_0}$ is a complex number that is computed based on measurements of incident light by the pixel at frequency $n\omega_0$ and that encodes phase and amplitude of light incident on the pixel; and (5) $\sphericalangle z_{n\omega_0}$ is the phase of $z_{n\omega_0}$. For example, there may be a separate complex number $z_{n\omega_0}$ for each different frequency of amplitude modulation in the sweep. In some cases, a computer may perform a conventional "four bucket" calculation (e.g., according to Equation 4) to calculate each complex number $z_{n\omega_0}$ in Equation 6. In some other cases, a computer may perform another conventional ToF calculation (which is not a "four bucket" method and is not according to Equation 4) to calculate each $z_{n\omega_0}$ in Equation 6.

In some cases, when performing calculations according to Equation 6: (1) a computer may calculate a vector z that consists of the elements $z_{n\omega_0}$ n=a, ..., N+a−1; and (2) a computer may calculate a vector $\sphericalangle z$ by taking the phase of vector z, such that each element of vector $\sphericalangle z$ is the phase of the corresponding element of vector z (e.g., such that, for any given n, $\sphericalangle z_{n\omega_0}$ in vector $\sphericalangle z$ is the phase of $z_{n\omega_0}$ in vector z).

The sigma notation in Equation 6 may represent a sum of terms, where each term is computed for a different frequency of amplitude modulation in a sweep. For example, in Equation 6, if a=0, and $\omega_0/2\pi$ is 1 MHz, and N=41, then the sweep of frequency is from 0 MHz to 40 MHz in increments of 1 MHz. Likewise, in Equation 6, if a=10, and $\omega_0/2\pi$ is 1 MHz, and N=41, then the sweep of frequency is from 10 MHz to 50 MHz in increments of 1 MHz.

In some implementations, in order to solve the non-linear least squares problem in Equation 6 or in Equation 13, a computer may perform a trust-region-based algorithm with least absolute residual criterion. For example, the trust-region-based algorithm may be as described in An Interior Trust Region Approach for Nonlinear Minimization Subject to Bounds, by T. Coleman et al., published in Society for Industrial and Applied Mathematics Journal, Vol. 6, No. 2, pp. 418-445, May 1996 (the "Coleman Paper"). However, this invention is not limited to a trust-region-based algorithm; other least square algorithms may be employed. Furthermore, this invention is not limited to least squares algorithms. For example, a computer may perform other fitting algorithms to solve for lifetime $\tau$ and depth d, or may calculate a closed form solution for lifetime $\tau$ and depth d.

Equation 6 assumes that the frequency of amplitude modulation is swept using equal intervals of frequency (e.g., frequency may be swept in increments of 1 MHz, for each discrete step in the sweep). Alternatively, this invention may be implemented, such that frequency is swept, where the increments in frequency are not constant (e.g., the frequency might increase by 1 MHz from the first to the second frequency of the sweep, and may increase by 2 MHz from the second to the third frequency in the sweep). In these alternative implementations (involving a sweep with non-equal increments of frequency), for each pixel of the ToF sensor, a computer may calculate scene depth d and fluorescence lifetime $\tau$ (of a scene point that corresponds to the pixel) by solving an optimization problem.

In an experiment, the accuracy of a prototype of this invention operating in periodic illumination mode was evaluated as follows: In this experiment, frequency of amplitude modulation of light was swept from 1 MHz to 40 MHz in increments of 1 MHz—that is, $\omega_0/2\pi$ was 1 MHz and ToF measurements were taken at equidistant intervals of frequency of amplitude modulation, such that the frequencies in the sweep were $n\omega_0$, n=1, 2, ..., 40. In this experiment, the ToF sensor took measurements at each frequency in the sweep. In this experiment, for each of ten pixels in the lock-in ToF sensor, the FLI system estimated fluorescence lifetime $\tau$ and distance d. In this experiment: (a) the average estimated lifetime $\bar{\tau}$ and average estimated distance $\bar{d}$, as estimated by the FLI system for the ten pixels, were 31.024 ns and 2.4961 m, respectively; and (b) the actual lifetime $\tau$ and actual distance d were 32 ns and 2.5 m, respectively. In this experiment, for these ten pixels: (a) the log scale root mean square error for the estimated lifetime $\tau$ ranged from −8.66 to −9.85; and (b) the signal-to-noise ratio ranged from 43.10 dB to 46.00 dB. Neither the prototype nor this experiment limit this invention. This invention is not limited to the prototype, it may be implemented in many other ways. This invention is not limited to the use scenario and technique used in this experiment, it may be implemented in many other ways.

Figure 2:
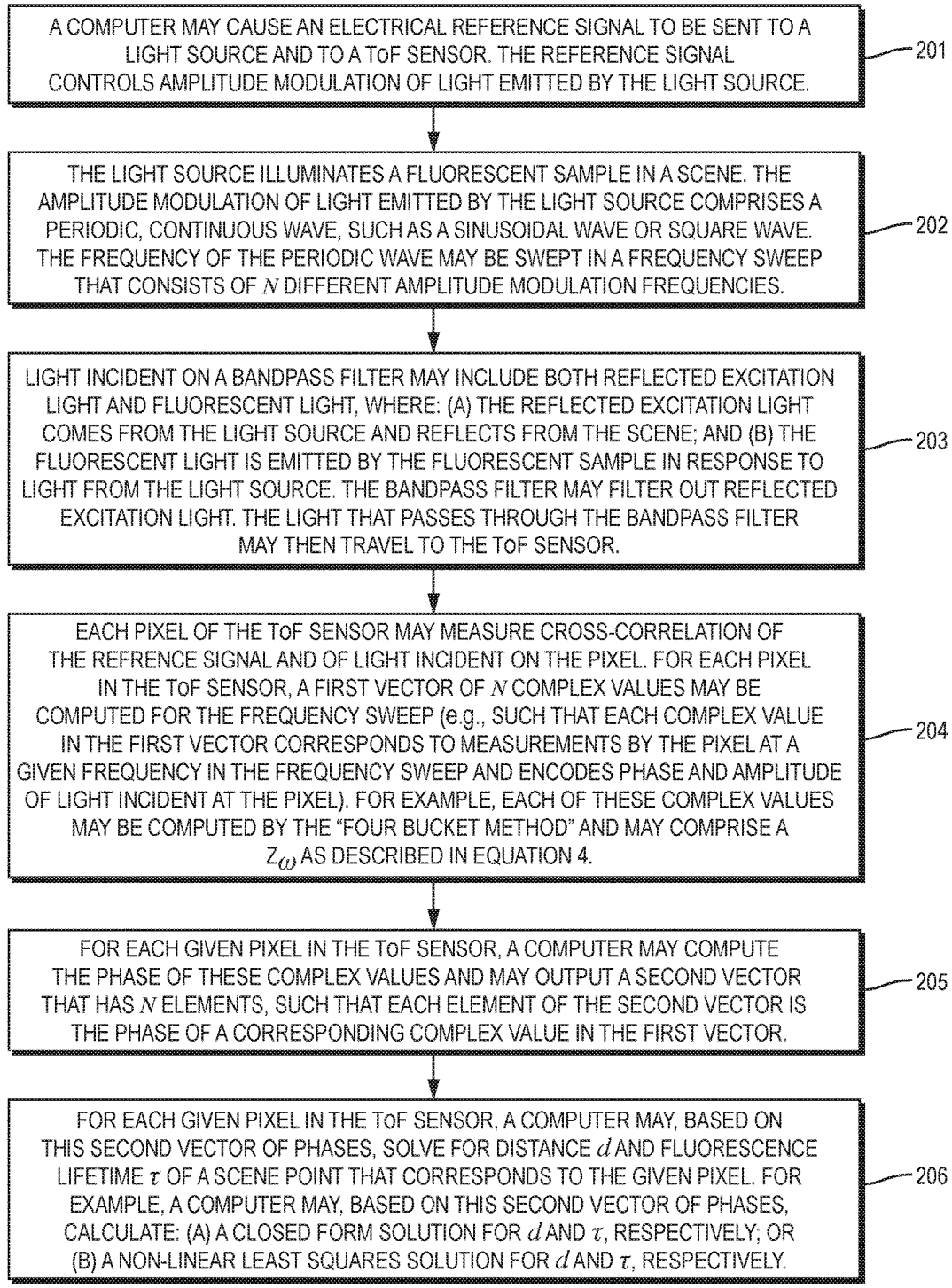
FIG. 2, FIG. 3, and FIG. 4 are flowcharts for FLI methods that employ a periodic waveform of amplitude-modulated light.

FIG. 2 is a flowchart for an FLI method that employs periodic amplitude-modulated light, in an illustrative implementation of this invention. In the example shown in FIG. 2, the method includes the following steps: A computer may cause an electrical reference signal to be sent to a light source and to a ToF sensor. The reference signal controls amplitude modulation of light emitted by the light source (Step 201). The light source illuminates a fluorescent sample in a scene. The amplitude modulation of light emitted by the light source comprises a periodic, continuous wave, such as a sine wave or square wave. The frequency of the periodic wave may be swept in a frequency sweep that consists of N different amplitude modulation frequencies (Step 202). Light incident on a bandpass filter may include both reflected excitation light and fluorescent light, where: (a) the reflected excitation light comes from the light source and reflects from the scene; and (b) the fluorescent light is emitted by the fluorescent sample in response to light from the light source. The bandpass filter may filter out reflected excitation light. The light that passes through the bandpass filter may then travel to the ToF sensor (Step 203). Each pixel of the ToF sensor may measure cross-correlation of the reference signal and of light incident on the pixel. For each pixel in the ToF sensor, a first vector of N complex values may be computed for the frequency sweep, such that each complex value in the first vector corresponds to measurements by the pixel at a given frequency in the frequency sweep and encodes phase and amplitude of light incident at the pixel. For example, each of these complex values may be computed by the "four bucket" method and may comprise a $z_\omega$ as described in Equation 4 (Step 204). For each pixel in the ToF sensor, a computer may compute phase of these complex values and may output a second vector that has N elements, such that each element of the second vector is the phase of a corresponding complex value in the first vector (Step 205). For each pixel in the ToF sensor, a computer may, based on this second vector of phases, solve for distance d and fluorescence lifetime $\tau$ of a scene point that corresponds to the pixel. For example, a computer may, based on this second vector of phases, calculate: (a) a closed form solution for d and $\tau$, respectively; or (b) a non-linear least squares solution for d and $\tau$, respectively (Step 206).

Figure 3:
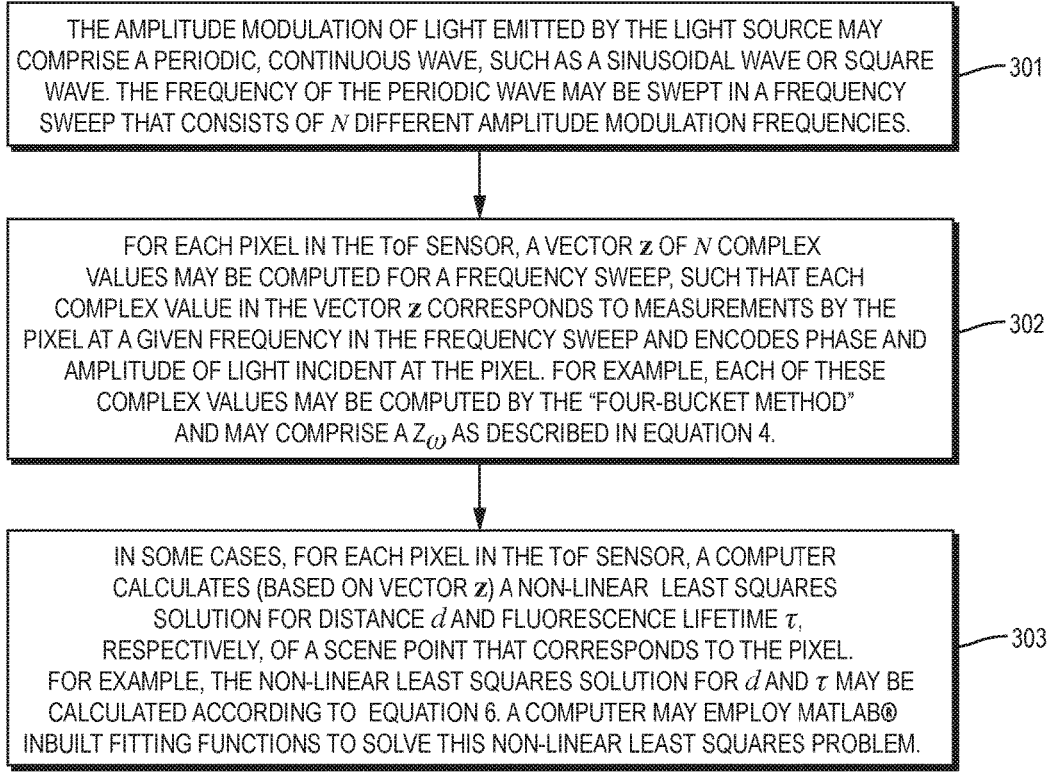

FIG. 3 is another flowchart for an FLI method that employs periodic amplitude-modulated light, in an illustrative implementation of this invention. In the example shown in FIG. 3, the method includes the following steps: The amplitude modulation of light emitted by the light source may comprise a periodic, continuous wave, such as a sine wave or square wave. The frequency of the periodic wave may be swept in a frequency sweep that consists of N different amplitude modulation frequencies (Step 301). For each pixel in the ToF sensor, a vector z of N complex values may be computed for a frequency sweep, such that each complex value in the vector z corresponds to measurements by the pixel at a given frequency in the frequency sweep and encodes phase and amplitude of light incident at the pixel. For example, each of these complex values may be computed by the "four bucket" method and may comprise a $z_\omega$ as described in Equation 4 (Step 302). For each pixel in the ToF sensor, a computer may calculate (based on vector z) a non-linear least squares solution for distance d and fluorescence lifetime $\tau$, respectively, of a scene point that corresponds to the given pixel. For example, the non-linear least squares solution for d and $\tau$ may be calculated according to Equation 6. A computer may employ Matlab® inbuilt fitting functions to solve this non-linear least squares problem (Step 303).

Figure 4:
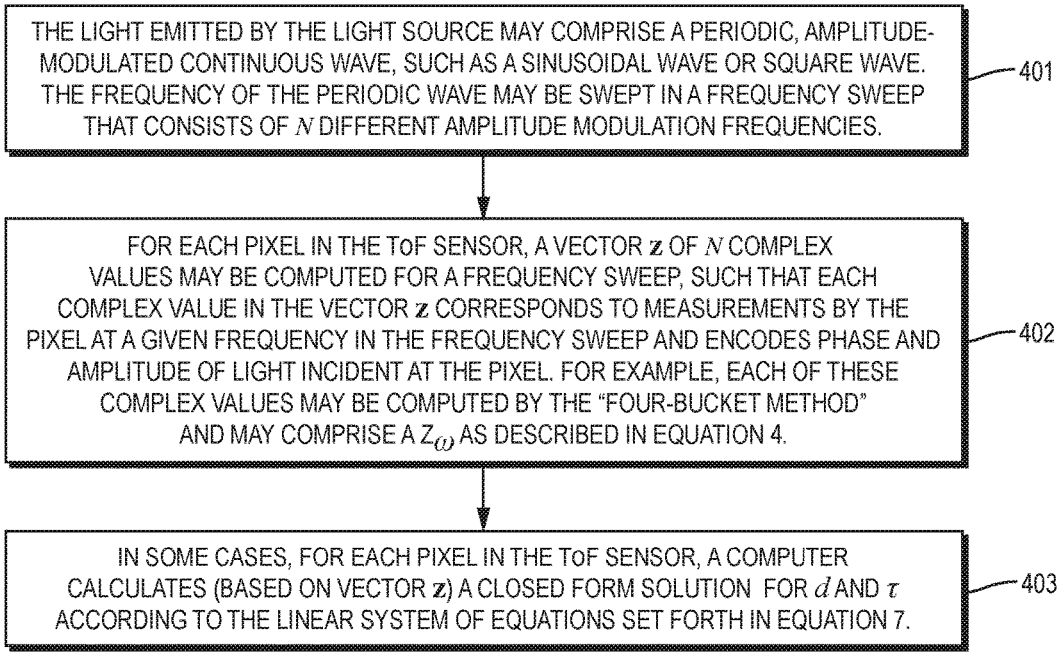

FIG. 4 is another flowchart of an FLI method that employs periodic amplitude-modulated light, in an illustrative implementation of this invention. In the example shown in FIG. 4, the method includes the following steps: The light emitted by the light source may comprise a periodic, amplitude-modulated continuous wave, such as a sinusoidal wave or square wave. The frequency of the periodic wave may be swept in a frequency sweep that consists of N different amplitude modulation frequencies (Step 401). For each pixel in the ToF sensor, a vector z of N complex values may be computed for a frequency sweep, such that each complex value in the vector z corresponds to measurements by the pixel at a given frequency in the frequency sweep and encodes phase and amplitude of light incident at the pixel. For example, each of these complex values may be computed by the "four bucket" method and may comprise a $z_\omega$, as described in Equation 4 (Step 402). In some cases: (a) for each pixel in the lock-in-ToF sensor, a computer may calculate (based on vector z) a closed form solution for distance d and fluorescence lifetime $\tau$, respectively of a scene point that corresponds to the given pixel; and (b) the closed form solution for d and $\tau$ may be calculated according to the linear system of equations $$z_{n+1}(1+j\omega_{n+1}\tau)=z_n(1+j\omega_n\tau)e^{-j\omega_0 2d/c} \quad \text{Equation 7}$$

where (1) the sweep comprises amplitude modulation frequencies $\omega_n$, (2) $\omega_n=n\omega_0$, (3) $\omega_0$ is a frequency of amplitude modulation, (4) n=a, a+1, a+2, . . . , N+a−1, (5) "a" is an integer that is greater than or equal to zero, (6) c is speed of light, and (7) each $z_n$ and $z_{n+1}$ is an element of the vector z (Step 403). For example, the linear system of equations in Equation 7 may be solved with any four contiguous integer values of n, such that $\ell \leq n \leq \ell+4$ where $\ell$ is an integer.

For example, in Step 403, if n=2, 3, 4, . . . 40, and $\omega_0/2\pi$ 1 MHz, then the sweep of frequency of amplitude modulation is from 2 MHz to 40 MHz, in increments of 1 MHz.

In some implementations, the ToF sensor mentioned in FIG. 2, FIG. 3, FIG. 4, FIG. 5 or FIG. 6 may comprise ToF sensor 105 (in FIG. 1).

Pulsed Illumination Mode

As noted above, in some implementations, the FLI system (e.g., 100) operates in a pulsed illumination mode. While operating in pulsed illumination mode, the light emitted by the light source (e.g., 115) may be an amplitude-modulated, coded, binary, pulsed, signal, where the amplitude modulation of the signal is not periodic. For example, while operating in pulsed illumination mode, the light emitted by the light source (e.g., 115) may comprise a maximum length sequence or a Gold sequence. For example, in some cases, the light signal emitted by the light source comprises a 31-bit MLS (maximum length sequence) described by the code MLS=0101110110001111100110100100001.

In some implementations, the FLI system operates in pulsed illumination mode and measures fluorescence lifetime and scene depth—even without precise knowledge of the shape of the pulsed light signal p(t) emitted by the system's light source (e.g., 115).

In some implementations, the measurements taken by the lock-in ToF sensor during pulsed illumination mode may be approximated as follows:

$$m(t) \approx \frac{1}{\Delta} \sum_{|n|\leq N_0} \hat{\phi}_n \hat{h}_n e^{j\omega_p nt} \quad \text{Equation 8}$$

where (1) j is a unit imaginary number that is equal to a square root of negative one, (2) $\Delta$ is signal length, (2) $\omega_p=2\pi/\Delta$, (3) $h_{Sf}(t)$ is the shift-invariant scene response; (4) $\hat{h}(\omega)$ is the Fourier transform of $h_{Sf}(t)$, (5) $\hat{h}_n=\hat{h}(\omega_p n)$, and (6) $\phi$ approximates the cross-correlation function (i.e., the cross-correlation of the reference electric signal and the light signal incident on the ToF sensor) with $2N_0+1$ Fourier series coefficients, $\hat{\phi}_n$, where $n=-N_0, \ldots, +N_0$. As used herein, "signal length" means number of samples times the amount of time that it takes to acquire one sample. As a non-limiting example: if the sample period is 1 ns and 100 samples are taken, then "signal length" is 100 ns.

In some implementations:

$$\hat{h}(\omega) = \int h(t)e^{-j\omega t}dt \text{ (FourierTransform)} \quad \text{Equation 9}$$

$$= \rho e^{-j\omega\left(\frac{2d}{c}\right)} + \frac{\mu}{\frac{1}{\tau}+j\omega} e^{-j\omega\left(\frac{2d}{c}\right)}$$

where (1) $\omega$ is angular frequency, (2) d is distance from scene (i.e., scene depth), (3) $\tau$ is fluorescence lifetime, (4) c is speed of light, (5) e is the unique number whose natural logarithm is equal to one, and thus e≈2.71828, (6) $\mu$ is luminance of fluorescence, and (7) $\rho$ is albedo. Alternatively, $\mu$ may be any other measure of intensity of fluorescent light.

In some implementations, $\hat{h}(\omega)$ may be expressed in polar form as $\hat{h}(\omega)=|\hat{h}(\omega)|e^{\angle \hat{h}(\omega)}$, where $$|\hat{h}(\omega)| = \sqrt{\frac{(\rho+\mu\tau)^2+(\omega\rho\tau)^2}{1+(\omega\tau)^2}} \quad \text{Equation 10}$$

$$\angle \hat{h}(\omega) = -\tan^{-1}\left(\frac{\omega\mu\tau^2}{\rho+\mu\tau+\rho(\omega\tau)^2}\right) - \frac{2d}{c}\omega \quad \text{Equation 11}$$

In some implementations: (1) light from the scene is filtered (e.g., by a dielectric, bandpass filter) to remove the reflected excitation light (i.e., to remove the amplitude-modulated light that was emitted by the light source and that reflected from the scene), so that only fluorescent emission light from the fluorescent sample is recorded by the ToF sensor; and thus, (2) $\rho=0$. Thus, in some implementations, by appropriately filtering the received light, Equation 11 simplifies to $$\angle \hat{h}(\omega) = -\tan^{-1}(\omega\tau) - \frac{2d\omega}{c}.$$

Note that in Equation 11, the phase $\angle \hat{h}(\omega)$ of the spectrum encodes both scene depth d and fluorescence lifetime $\tau$.

In vector-matrix notation, the discretized system of equations in Equation 8 may be written as $$m=VD_{\hat{\phi}}\hat{h} \quad \text{Equation 12}$$

where (1) m is K×1 vector of discretized ToF sensor measurements $m_k=m(kT_s), k \in [0, K-1]$, (2) $T_s$ is sampling period, (3) V is a Vandermonde matrix of size K×(2$N_0$+1) with matrix element $[V]_{k,n}=e^{j(2\pi/\Delta)T_s nk}$, $n \in [-N_0, +N_0]$, (4) $D_{\hat{\phi}}$ is a (2$N_0$+1)×(2$N_0$+1) diagonal matrix with diagonal entries $[D]_{n,n}=\hat{\phi}_n$, and (5) $\hat{h}$ is a (2$N_0$+1)×1 vector of the discretized spectrum (see Equation 9) with entries $\hat{h}(2\pi n/\Delta)$, $n=-N_0, \ldots, N_0$.

Thus, in some implementations, the estimation problem is: given K measurements m, estimate scene depth d and fluorescence lifetime τ.

In illustrative implementations, the emitted light signal and the reference signal applied to the lock-in ToF sensor may be the same except for delays. The lock-in ToF sensor may take measurements that effectively cross-correlate these two signals.

In some implementations of this invention, in which the FLI system is operating in pulsed illumination mode: (1) the cross-correlation ϕ(t) is a real, time symmetric function; (2) thus the matrix $D_{\tilde{\phi}}$ does not contribute to the phase of vector ĥ in Equation 12; (3) phase may, in turn, encode the scene depth and fluorescence lifetime parameters, see discussion of Equation 11; (4) thus the matrix $D_{\tilde{\phi}}$ (which does not contribute to phase in Equation 12) may be disregarded, when calculating the lifetime and depth parameters from phase; and (5) cross-correlation function ϕ(t)—and the light waveform p(t) that is being cross-correlated with the reference signal—do not need to be known in order to calculate phase according to Equation 12 and to extract depth and lifetime from phase.

In some implementations of this invention (in which the FLI system is operating in pulsed illumination mode), the phase, lifetime and depth parameters are extracted from the same set of ToF sensor measurements. Specifically, in some implementations in which the FLI system is operating in pulsed illumination mode: (a) phase is extracted from a set of ToF sensor measurements; (b) fluorescence lifetime and scene depth are calculated based on the phase; and (c) thus the phase, lifetime and scene depth are extracted from the same set of ToF sensor measurements. This is in contrast to conventional FLI, in which phase of the amplitude modulation may be known in advance by separate calibration measurements, and this known phase may be used to help extract fluorescence lifetime from a later, separate set of ToF sensor measurements.

Furthermore, in some implementations of this invention (in which the FLI system is operating in pulsed illumination mode), the amplitude of the modulation of the illumination light signal is not known in advance from separate calibration measurements, but instead the phase, lifetime, depth and amplitude may be extracted from the same set of ToF sensor measurements. This is in contrast to conventional FLI, in which the precise amplitude of the modulation may be known in advance.

In some implementations, in which the FLI system is operating in pulsed illumination mode: (a) a computer may perform a Discrete Fourier Transform (DFT) on the vector of measurements m for that pixel, resulting in vector g for that pixel, such that each element of vector g is a complex value that encodes both amplitude and phase of light incident on that pixel, and (b) a computer may extract depth d and fluorescence lifetime τ from vector g by solving a non-linear least squares problem or other non-linear inverse problem. For example, a computer may determine d and τ by solving a non-linear least squares problem according to:

$$\underset{\{d,\tau\}}{\operatorname{argmin}} \sum_{k=0}^{K-1} \left| \sphericalangle g_k + 2\left(\frac{d}{c}\right) k\omega_p + \tan^{-1}(k\omega_p \tau) \right|^2 \quad \text{Equation 13}$$

where (1) K is the number of elements in vector g, (2) $\omega_p = 2\pi/\Delta$, (3) Δ is signal length, (4) c is speed of light, (5) each element $g_k$ of the vector g is a complex number that corresponds to measurement of incident light by the pixel at a different time during the pulsed signal, and (6) $\sphericalangle g_k$ is the phase of $g_k$.

In some cases, when performing calculations according to Equation 13, a computer may calculate a vector $\sphericalangle g$ by taking the phase of vector g, such that each element of vector $\sphericalangle g$ is the phase of the corresponding element of vector g (e.g., for any given k, $\sphericalangle g_k$ in vector $\sphericalangle g$ is the phase of $g_k$ in vector g).

In some implementations, to solve the non-linear least squares problem in Equation 13, a computer may perform a trust-region-based algorithm with least absolute residual criterion. For example, a computer may perform a trust-region-based algorithm described in the Coleman Paper.

Figure 5:
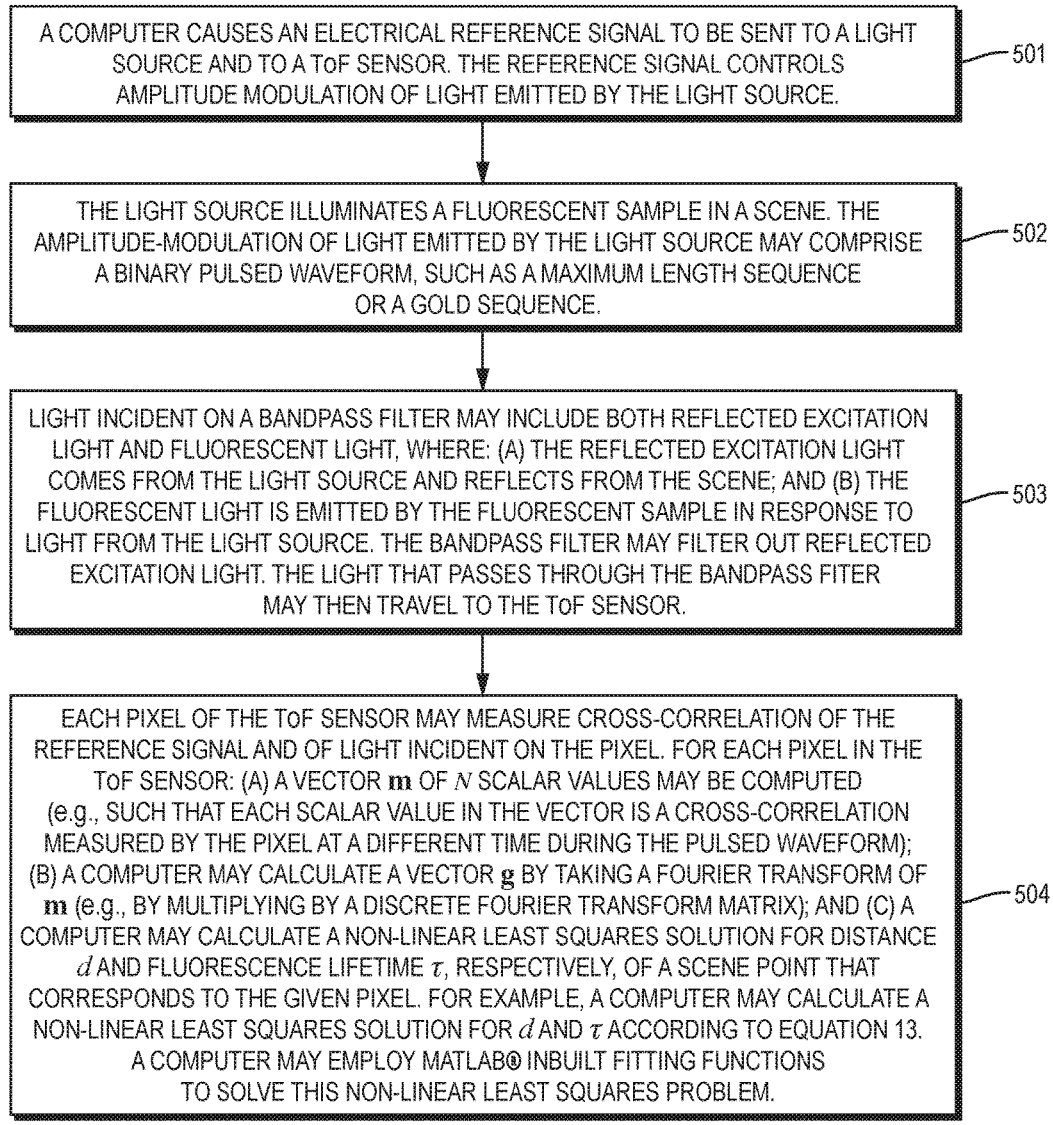
FIG. 5 is a flowchart for an FLI method that employs pulsed light.

FIG. 5 is a flowchart for an FLI method that employs pulsed modulation of light, in an illustrative implementation of this invention. In the example shown in FIG. 5, the method includes the following steps: A computer causes an electrical reference signal to be sent to a light source and to a ToF sensor. The reference signal controls amplitude modulation of light emitted by the light source (Step 501). The light source illuminates a fluorescent sample in a scene. The amplitude modulation of light emitted by the light source may comprise a binary pulsed waveform, such as a maximum length sequence or a Gold sequence (Step 502). Light incident on a bandpass filter may include both reflected excitation light and fluorescent light, where: (a) the reflected excitation light comes from the light source and reflects from the scene; and (b) the fluorescent light is emitted by the fluorescent sample in response to light from the light source. The bandpass filter may filter out reflected excitation light. The light that passes through the bandpass filter may then travel to the ToF sensor (Step 503). Each pixel of the ToF sensor may measure cross-correlation of the reference signal and of light incident on the pixel. For each pixel in the ToF sensor: (a) a vector m of N scalar values may be computed (e.g., such that each scalar value in the vector is a cross-correlation measured by the pixel at a different time during the pulsed waveform); (b) a computer may calculate a vector g by taking a Fourier transform of m (e.g., by multiplying by a discrete Fourier transform matrix); and (c) a computer may calculate a non-linear inverse solution for distance d and fluorescence lifetime τ, respectively, of a scene point that corresponds to the given pixel. For example, a computer may calculate a non-linear least squares solution for d and τ according to Equation 13. A computer may employ Matlab® inbuilt fitting functions to solve this non-linear least squares problem (Step 504).

As noted above, conventional FLI devices suffer from at least two technological problems which may be solved by this invention. In addition, some conventional FLI devices suffer from a third technological problem: Specifically, for some conventional FLI devices, fluorescence lifetime must be known (e.g., from calibration) in order to solve for scene depth. This invention may solve this third technological problem also, because, in illustrative implementations of this invention, an FLI system may—without calibration to determine fluorescence lifetime—accurately measure both fluorescence lifetime and depth.

Applications

In illustrative implementations of this invention, the FLI system has many practical applications. For example, in some implementations of this invention, the FLI system is employed for: (a) microscopy, including both wide-field microscopy and point-scanning microscopy; (b) biological imaging, including estimation of a fluorescence lifetime that is less than one millisecond and more than one picosecond; (c) estimation of fluorescence lifetime for large-scale (macroscopic) scenes; and (d) detection of counterfeit banknotes, based on fluorescent characteristics of the banknotes.

In some implementations of this invention, the FLI system is well-suited for imaging at both a large scale and a small scale. This is because, among other things, the FLI system may determine depth and fluorescence lifetime on a per-pixel basis, regardless of the lateral scale of the scene being imaged.

FIG. 6 shows an FLI method, in an illustrative implementation of this invention. In the example shown in FIG. 6, the method includes the following step: Based on measurements taken by a ToF sensor, a computer may, among other things: (a) calculate, for each given pixel in the ToF sensor, distance d and fluorescence lifetime τ, respectively, of a scene point that corresponds to the given pixel; (b) output an amplitude image; (c) output a phase image; (d) output a depth map; (e) output a fluorescence lifetime map; or (f) identify one or more materials (e.g., fluorescent materials) in the scene (Step 601).

Prototype: Source Code

In the Computer Program Listing above, three computer program files are listed. These three computer program files comprise software employed in a prototype implementation of this invention. To run these as Matlab® software files, the filename extension for these files would be changed from ".txt" to ".m", ".mat", and ".m", respectively. Here is a description of these three computer program files:

(1) OpticaDataProcess.txt: OpticaDataProcess is a function that: (a) takes, as an input, a vector of complex-valued measurements acquired by a lock-in ToF sensor; (b) unwraps phases of the complex-valued measurements, (c) performs a non-linear fit by calling the createFit function, and (d) outputs fluorescence lifetime in nanoseconds and distance (scene depth) in meters.

(2) createFit.txt: The createFit program performs a non-linear fit.

(3) FDToF_optica.txt: FDToF_optica is a function that: (a) takes, as inputs, depth and lifetime data outputted by the OpticaDataProcess function; (b) calculates other metrics (root-mean-square-error and signal-to-noise ratio), and (c) outputs a table of the lifetime and depth data and of the other metrics.

This invention is not limited to the software set forth in these three program files. Other software may be employed. Depending on the particular implementation, the software used in this invention may vary.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, hardware components of an FLI system, including any ToF sensor, driver, light source, or ADC; (2) to perform a DFT; (3) to perform a "4-bucket" algorithm; (4) to calculate, based on ToF sensor measurements, a vector of complex values that encode phase and amplitude of incident light; (5) to extract lifetime fluorescence and scene depth from phase; (6) to perform any other calculation, computation, program, algorithm, or computer function described or implied above; (7) to receive signals indicative of human input; (8) to output signals for controlling transducers for outputting information in human perceivable format; and (9) to process data, to perform computations, to execute any algorithm or software, and to control the read or write of data to and from memory devices (items 1-9 of this sentence referred to herein as the "Computer Tasks"). The one or more computers (e.g. 103, 133) may be in any position or positions within or outside of the FLI system. For example, in some cases (a) at least one computer is housed in or together with other components of the FLI system, such as the ToF sensor or illumination system, and (b) at least one computer is remote from other components of the FLI system. The one or more computers may communicate with each other or with other devices either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Network Communication

In illustrative implementations of this invention, an electronic device (e.g., 103, 105, 111, 131, 135) is configured for wireless or wired communication with other electronic devices in a network.

For example, in some cases, one or more components of the FLI system (e.g., 100) may each include a wireless communication module for wireless communication with other electronic devices in a network. Each wireless communication module may include (a) one or more antennas, (b) one or more wireless transceivers, transmitters or receivers, and (c) signal processing circuitry. Each wireless communication module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables or wiring.

In some cases, one or more computers (e.g., 103, 133) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

To compute "based on" specified data means to perform a computation that takes the specified data as an input.

Here are some non-limiting examples of a "camera": (a) a digital camera; (b) a digital grayscale camera; (c) a digital color camera; (d) a video camera; (e) a light sensor or image sensor; (f) a set or array of light sensors or image sensors; (g) an imaging system; (h) a light field camera or plenoptic camera; (i) a time-of-flight camera; and (j) a depth camera. A camera includes any computers or circuits that process data captured by the camera.

To say that a computer "causes" a device to do an action means that the computer outputs one or more signals that directly or indirectly control the device and that thereby cause the device to do the action.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. The term "computer" also includes any analog computer. However, a human is not a "computer", as that term is used herein.

As used herein, to say that a scene point "corresponds" to a pixel means that light which reflects from the scene point is focused at the pixel. As used herein, to say that a period of time "corresponds" to a complex number means that the complex number is calculated based on measurements taken during the period of time. As used herein, to say that a frequency "corresponds" to a complex number means that the complex number is calculated based on measurements taken at that frequency.

"Defined Term" means a term or phrase that is set forth in quotation marks in this Definitions section.

Unless the context clearly indicates otherwise, the terms "depth", "scene depth" and "distance" each mean distance between a ToF sensor and a point in a scene that is being imaged by the ToF sensor.

For an event to occur "during" a time period, it is not necessary that the event occur throughout the entire time period. For example, an event that occurs during only a portion of a given time period occurs "during" the given time period.

The term "e.g." means for example.

Each equation above is referred to herein by the equation number set forth to the right of the equation. For example: "Equation 6" means Equation 6 above; "Equation 7" means Equation 7 above; and "Equation 13" means Equation 13 above. Non-limiting examples of an "equation", as that term is used herein, include: (a) an equation that states an equality; (b) an inequation that states an inequality (e.g., that a first item is greater than or less than a second item); (c) a mathematical statement of proportionality or inverse proportionality; and (d) a system of equations.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"FLI" means fluorescence lifetime imaging.

"For instance" means for example.

Unless the context clearly indicates otherwise, "frequency" means frequency of amplitude modulation of light.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

To say that a calculation is "according to" a first equation means that the calculation includes (a) solving the first equation; or (b) solving a second equation, where the second equation is derived from the first equation. Non-limiting examples of "solving" an equation include solving the equation in closed form or by numerical approximation or by optimization.

The term "include" (and grammatical variations thereof) shall be construed as if followed by "without limitation".

"Intensity" means any measure of intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure, radiant energy density, luminance or luminous intensity.

"I/O device" means an input/output device. Non-limiting examples of an I/O device include a touch screen, other electronic display screen, keyboard, mouse, microphone, handheld electronic game controller, digital stylus, display screen, speaker, or projector for projecting a visual display.

A non-limiting example (in the context of an algorithm) of X not being not "known" in advance, is that X is not an input to the algorithm. For purposes of the preceding sentence, a value that is computed by the algorithm is not an "input" to the algorithm, even if the algorithm, after computing the value, uses the value in a subsequent step of the algorithm.

Unless the context clearly indicates otherwise, the term "lifetime" means "fluorescence lifetime". A non-limiting example of measuring fluorescence lifetime is measuring average fluorescence lifetime.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

"Listed patents" means U.S. Pat. Nos. 6,777,659; 6,825,455; 7,012,738; 8,294,882; 6,323,942; 6,515,740; 6,587,186; 7,405,812; 7,719,662; 8,194,233; 8,314,924; 8,953,149; 6,678,039; 7,060,957; 7,636,150; 8,786,678; 7,361,883; 7,408,627; 9,516,244; 7,671,391; 7,262,402; and 8,355,117. A "Listed patent" means one of the Listed patents. The entire disclosure of each of the Listed patent is hereby incorporated by reference herein. The entire disclosure of a Listed patent includes the specification and drawings of the Listed patent, but does not include the patent claims of the Listed patent.

As used herein, (i) a single scalar is not a "matrix", and (ii) one or more entries, all of which are zero (i.e., a so-called null matrix), is not a "matrix".

To "multiply" includes to multiply by an inverse. Thus, to "multiply" includes to divide.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

The "phase of the complex numbers" means the phase of each of the complex numbers, respectively.

"Scene point" means a location in a scene. As used herein, fluorescence lifetime "of" a scene point means lifetime of fluorescence that occurs at the scene point.

As used herein, the term "set" does not include a group with no elements. Mentioning a first set and a second set does not, in and of itself, create any implication regarding whether or not the first and second sets overlap (that is, intersect).

Unless the context clearly indicates otherwise, "some" means one or more.

As used herein, a "subset" of a set consists of less than all of the elements of the set.

The term "such as" means for example.

As used herein, the term "sweep" of frequencies does not imply any order of frequencies or direction of change in frequency. Here are some non-limiting examples: (a) a "sweep" may be from highest to lowest frequency, or from lowest to highest frequency; (b) frequencies in a "sweep" may be monotonically increasing, monotonically decreasing, monotonically weakly decreasing, monotonically weakly increasing or none of the above; (c) a given frequency may repeat more than once in a sweep, either consecutively or separated by one or more other frequencies; and (d) in a sweep of frequencies which includes a highest frequency, a middle frequency and a lowest frequency, these frequencies may occur in any order, such as middle, then highest, then lowest.

To say that a machine-readable medium is "transitory" means that the medium is a transitory signal, such as an electromagnetic wave.

A non-limiting example of a "vector" is a one-dimensional array. (Without affecting this definition in any way, we note that this meaning is common in computer science).

A matrix may be indicated by a bold capital letter (e.g., D). A vector may be indicated by a bold lower case letter (e.g., a). However, the absence of these indicators does not indicate that something is not a matrix or not a vector.

Unless the context clearly indicates otherwise, a math expression that symbolizes a sequence of numbers in the form n=a, . . . , Y means a sequence of integers that starts with integer a and ends with integer Y, where each element of the sequence (except the first element of the sequence) is equal to the preceding element in the sequence plus 1. For example: (a) n=0, . . . , 2 means n=0, 1, 2; (b) x=0, . . . , 3 means x=0, 1, 2, 3; and (c) g=0, . . . , 5 means g=0, 1, 2, 3, 4, 5.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

VARIATIONS

This invention may be implemented in many different ways. Here are some non-limiting examples:

In some implementations, this invention is a method comprising: (a) a light source illuminating a scene with amplitude-modulated light, such that (i) amplitude modulation of the light is periodic, and (ii) frequency of the amplitude modulation is swept in a sweep; (b) a time-of-flight sensor taking measurements of light incident on the sensor, which incident light includes light that has reflected from the scene and includes fluorescent light that has been emitted by fluorescent material in the scene; and (c) one or more computers performing a set of calculations that includes, for each given pixel in a set of pixels in the time-of-flight sensor (i) calculating a vector of complex numbers, such that each of the complex numbers, respectively, encodes phase and amplitude of light incident at the given pixel and is calculated based on measurements taken by the given pixel at a given frequency of amplitude modulation of the sweep, which given frequency does not correspond to any other complex number in the vector, and (ii) calculating, based on phase of the complex numbers, fluorescence lifetime of a scene point that corresponds to the given pixel. In some cases, the calculating of fluorescence lifetime, based on phase of the complex numbers, comprises solving a non-linear least squares problem. In some cases, the calculating of fluorescence lifetime, based on phase of the complex numbers, comprises solving a non-linear least squares problem according to Equation 6. In some cases, the calculating of fluorescence lifetime, based on phase of the complex numbers, comprises computing a closed form solution. In some cases, the calculating of fluorescence lifetime, based on phase of the complex numbers, comprises computing a closed form solution according to a linear system of equations. In some cases, the calculating of fluorescence lifetime, based on phase of the complex numbers, comprises computing a closed form solution according to Equation 7. In some cases, the set of calculations for the given pixel includes calculating, based on phase of the complex numbers, scene depth of a scene point that corresponds to the given pixel. In some cases, for a given pixel, the one or more computers calculate, based on phase of the complex numbers, both depth of the scene point and lifetime fluorescence of the scene point by solving the non-linear least squares problem. In some cases, for a given pixel, the one or more computers calculate, based on phase of the complex numbers, both depth of the scene point and lifetime fluorescence of the scene point by solving the non-linear least squares problem according to Equation 6. In some cases, for a given pixel, the one or more computers calculate, based on phase of the complex numbers, a closed form solution for both depth of the scene point and lifetime fluorescence of the scene point. In some cases, for a given pixel, the one or more computers calculate, based on phase of the complex numbers, a closed form solution for both depth of the scene point and lifetime fluorescence of the scene point, according to a linear system of equations. In some cases, for a given pixel, the one or more computers calculate, based on phase of the complex numbers, a closed form solution for both depth of the scene point and lifetime fluorescence of the scene point, according to Equation 7. Each of the cases described above in this paragraph is an example of the method described in the first sentence of this paragraph, and is also an example of an embodiment of this invention that may be combined with other embodiments of this invention.

In some implementations, this invention is a system comprising: (a) a light source; (b) a lock-in time-of-flight sensor; and (c) one or more computers that are programmed (i) to cause the light source to illuminate a scene with amplitude-modulated light, such that (A) amplitude modulation of the light is periodic, and (B) frequency of the amplitude modulation is swept in a sweep, (ii) to cause the time-of-flight sensor to take measurements of light incident on the sensor, which incident light includes light that has reflected from the scene and includes fluorescent light that has been emitted by fluorescent material in the scene, and (iii) to perform a set of calculations that includes, for each given pixel in a set of pixels in the time-of-flight sensor (A) calculating a vector of complex numbers, such that each of the complex numbers, respectively, encodes phase and amplitude of light incident at the given pixel and is calculated based on measurements taken by the given pixel at a given frequency of amplitude modulation of the sweep, which given frequency does not correspond to any other complex number in the vector, and (B) calculating, based on phase of the complex numbers, fluorescence lifetime of a scene point that corresponds to the given pixel. In some cases, the calculating of fluorescence lifetime, based on phase of the complex numbers, comprises solving a non-linear least squares problem. In some cases, the calculating of fluorescence lifetime, based on phase of the complex numbers, comprises solving a non-linear least squares problem according to Equation 6. In some cases, the calculating of fluorescence lifetime, based on phase of the complex numbers, comprises computing a closed form solution. In some cases, the calculating of fluorescence lifetime, based on phase of the complex numbers, comprises computing a closed form solution according to a linear system of equations. In some cases, the calculating of fluorescence lifetime, based on phase of the complex numbers, comprises computing a closed form solution according to Equation 7. In some cases, the set of calculations for the given pixel includes calculating, based on phase of the complex numbers, scene depth of a scene point that corresponds to the given pixel. In some cases, for the given pixel, the one or more computers calculate, based on phase of the complex numbers, a closed form solution for both depth of the scene point and lifetime fluorescence of the scene point, according to Equation 7. Each of the cases described above in this paragraph is an example of the system described in the first sentence of this paragraph, and is also an example of an embodiment of this invention that may be combined with other embodiments of this invention.

Each description above of any method or apparatus of this invention describes a non-limiting example of this invention. This invention is not limited to those examples, and may be implemented in other ways.

Each description above of any implementation, embodiment or case of this invention (or any use scenario for this invention) describes a non-limiting example of this invention. This invention is not limited to those examples, and may be implemented in other ways.

Each Figure that illustrates any feature of this invention shows a non-limiting example of this invention. This invention is not limited to those examples, and may be implemented in other ways.

The Provisional Application does not limit the scope of this invention. The Provisional Application describes non-limiting examples of this invention, which examples are in addition to—and not in limitation of—the implementations of this invention that are described in the main part of this document. For example, if any given feature described in the Provisional Application is different from, or in addition to, the features described in the main part of this document, this additional or different feature of the Provisional Application does not limit any implementation of this invention described in the main part of this document, but instead merely describes another example of this invention. As used herein, the "main part of this document" means this entire document (including any drawings listed in the Brief Description of Drawings above and any software file listed in the Computer Program Listing section above), except that the "main part of this document" does not include any document that is incorporated by reference herein.

Any document that is incorporated by reference herein ("incorporated document") does not limit the scope of this invention (including the scope of any hardware, hardware component, method, process, step, software, algorithm, feature, or technology that is described in the main part of this document). For example, if any given feature described in any incorporated document is different from, or in addition to, the features described in the main part of this document, this additional or different feature of the incorporated document does not limit any implementation of this invention described in the main part of this document.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the implementations (including hardware, hardware components, methods, processes, steps, software, algorithms, features, or technology) that are described or incorporated by reference herein.

What is claimed is:

1. A method comprising:
   (a) illuminating a scene with amplitude-modulated light, in such a way that
      (i) amplitude modulation of the light is periodic, and
      (ii) frequency of the amplitude modulation is swept in a sweep;
   (b) taking measurements, with a time-of-flight sensor, of light incident on the sensor, which incident light includes light that has reflected from the scene and includes fluorescent light that has been emitted by fluorescent material in the scene; and
   (c) performing, with one or more computers, calculations that include, for each given pixel in a set of pixels in the time-of-flight sensor
      (i) calculating a vector of complex numbers, in such a way that each of the complex numbers, respectively, encodes phase and amplitude of light incident at the given pixel and is calculated based on measurements taken by the given pixel at a given frequency of amplitude modulation of the sweep, which given frequency does not correspond to any other complex number in the vector, and
      (ii) calculating, based on phase of the complex numbers, fluorescence lifetime of a scene point that corresponds to the given pixel;
   wherein the calculating of fluorescence lifetime, based on phase of the complex numbers, comprises computing a closed form solution according to Equation 7.

2. The method of claim 1, wherein, for the given pixel, the one or more computers calculate, based on phase of the complex numbers, a closed form solution for both depth of the scene point and lifetime fluorescence of the scene point, according to Equation 7.

3. A system comprising:
   (a) a light source;
   (b) a lock-in time-of-flight sensor; and
   (c) one or more computers that are programmed
      (i) to cause the light source to illuminate a scene with amplitude-modulated light, in such a way that
         (A) amplitude modulation of the light is periodic, and
         (B) frequency of the amplitude modulation is swept in a sweep,
      (ii) to cause the time-of-flight sensor to take measurements of light incident on the sensor, which incident light includes light that has reflected from the scene and includes fluorescent light that has been emitted by fluorescent material in the scene, and
      (iii) to perform a set of calculations that includes, for each given pixel in a set of pixels in the time-of-flight sensor
         (A) calculating a vector of complex numbers, in such a way that each of the complex numbers, respectively, encodes phase and amplitude of light incident at the given pixel and is calculated based on measurements taken by the given pixel at a given frequency of amplitude modulation of the sweep, which given frequency does not correspond to any other complex number in the vector, and
         (B) calculating, based on phase of the complex numbers, fluorescence lifetime of a scene point that corresponds to the given pixel;
   wherein the calculating of fluorescence lifetime, based on phase of the complex numbers, comprises computing a closed form solution according to Equation 7.

4. A system comprising:
   (a) a light source;
   (b) a lock-in time-of-flight sensor; and
   (c) one or more computers that are programmed
      (i) to cause the light source to illuminate a scene with amplitude-modulated light, in such a way that
         (A) amplitude modulation of the light is periodic, and
         (B) frequency of the amplitude modulation is swept in a sweep,
      (ii) to cause the time-of-flight sensor to take measurements of light incident on the sensor, which incident light includes light that has reflected from the scene and includes fluorescent light that has been emitted by fluorescent material in the scene, and
      (iii) to perform a set of calculations that includes, for each given pixel in a set of pixels in the time-of-flight sensor
         (A) calculating a vector of complex numbers, in such a way that each of the complex numbers, respectively, encodes phase and amplitude of light incident at the given pixel and is calculated based on measurements taken by the given pixel at a given frequency of amplitude modulation of the sweep, which given frequency does not correspond to any other complex number in the vector, and (B) calculating, based on phase of the complex numbers, fluorescence lifetime of a scene point that corresponds to the given pixel;

wherein, for the given pixel, the one or more computers calculate, based on phase of the complex numbers, a closed form solution for both depth of the scene point and lifetime fluorescence of the scene point, according to Equation 7.

\* \* \* \* \*